United States Patent
Shirado et al.

(10) Patent No.: US 6,860,884 B2
(45) Date of Patent: Mar. 1, 2005

(54) IMPLANT FOR BONE CONNECTOR

(75) Inventors: Osamu Shirado, Hokkaido (JP); Kazuya Oribe, Tokyo (JP); Hiroshi Takamido, Aichi-ken (JP)

(73) Assignee: Showa Ika Kohgyo Co., Ltd., Aichi-Ken (JP)

( * ) Notice: Subject to any disclaimer, the term of this patent is extended or adjusted under 35 U.S.C. 154(b) by 87 days.

(21) Appl. No.: 10/207,885

(22) Filed: Jul. 31, 2002

(65) Prior Publication Data

US 2003/0109881 A1 Jun. 12, 2003

(30) Foreign Application Priority Data

Aug. 1, 2001 (JP) ........................................ 2001-233512

(51) Int. Cl.[7] .......................... A61B 17/56; A61B 17/58; A61F 2/30
(52) U.S. Cl. .......................................... 606/61; 606/72
(58) Field of Search .............................. 606/60, 61, 72, 606/73; 24/342.1, 343, 378.1, 379.1, 527

(56) References Cited

U.S. PATENT DOCUMENTS

| | | | |
|---|---|---|---|
| 4,085,744 A | | 4/1978 | Lewis et al. |
| 5,201,734 A | * | 4/1993 | Cozad et al. .................. 606/62 |
| 5,415,659 A | * | 5/1995 | Lee et al. ...................... 606/61 |
| 5,439,463 A | * | 8/1995 | Lin .............................. 606/61 |
| 5,487,744 A | * | 1/1996 | Howland ....................... 606/61 |
| 5,527,314 A | * | 6/1996 | Brumfield et al. ............. 606/61 |
| 5,676,665 A | * | 10/1997 | Bryan .......................... 606/61 |
| 6,050,997 A | * | 4/2000 | Mullane ....................... 606/61 |
| 6,077,263 A | | 6/2000 | Ameil et al. |
| 6,238,396 B1 | * | 5/2001 | Lombardo .................... 606/61 |
| 6,352,537 B1 | * | 3/2002 | Strnad ......................... 606/61 |
| 6,416,515 B1 | * | 7/2002 | Wagner ........................ 606/61 |
| 6,485,491 B1 | * | 11/2002 | Farris et al. .................. 606/61 |
| 2002/0169451 A1 | * | 11/2002 | Yeh ............................. 606/61 |

FOREIGN PATENT DOCUMENTS

| | | |
|---|---|---|
| FR | 2662073 | 11/1991 |
| FR | 2684866 | 6/1993 |
| FR | 2695550 | 3/1994 |
| FR | 2752719 | 3/1998 |
| GB | 2269753 | 2/1994 |
| JP | 9-285473 | 11/1997 |
| JP | 11089854 | 4/1999 |
| JP | 11347046 | 12/1999 |
| NL | 1011260 | 8/2000 |

OTHER PUBLICATIONS

"Vertebral Instrumentation", by Sato et al., Medical View, published on May 1, 2002, pp. 63–65 76–79, and 83–85, with a partial English language translation.
English Language Abstract of JP 9–285473.
English Language Abstract of JP 11–347046.

* cited by examiner

Primary Examiner—Eduardo C. Robert
Assistant Examiner—Anu Ramana
(74) Attorney, Agent, or Firm—Greenblum & Bernstein, P.L.C.

(57) ABSTRACT

An implant for a bone connector includes an implant body, a hook portion, a fixing clamp and a movable clamp. The fixing clamp has a curved shape and supports a vertebral arch of a vertebra by grasping the vertebral arch. The implant body is provided on an upper portion of the fixing clamp. The hook portion over which a connecting member is hooked is provided on an upper portion of the implant body. Further, the movable clamp, which has a curved shape and grasps the vertebral arch, is provided on the upper portion of the implant body and is disposed to be opposed to the fixing clamp.

5 Claims, 4 Drawing Sheets

IMPLANT FOR BONE CONNECTOR

CROSS REFERENCE TO RELATED APPLICATION

This application claims benefit of priority under 35 U.S.C. §119 to Japanese Patent Application No. 2001-233512, filed on Aug. 1, 2001, the entire contents of which are incorporated by reference herein.

BACKGROUND OF THE INVENTION

1. Field of the Invention

The present invention relates to an implant for a bone connector used for connecting bones.

2. Description of the Related Art

When connecting bones such as thoracic vertebrae or lumbar vertebrae, the following method has been conventionally employed. A first implant 3 is screwed into centrum 1 such as the thoracic vertebra and the lumbar vertebra. A second implant 4 is screwed into centrum 2. A connecting rod 5 connects the first implant 3 to the second implant 4 as shown in FIG. 1.

The first implant 3 includes a screw portion and a head portion. The screw portion is screwed into centrum and the head portion with a large diameter has a rod engaging groove. Also, the second implant 4 includes the same conformation. Since end portions of the connecting rod 5 are fixed to the rod engaging groove of the first implant 3 and that of the second implant 4 respectively, the connecting rod 5 is integrally fixed to the first implant 3 and the second implant 4 and accordingly a bone connector is formed.

Further, an implant 9 is screwed into centrum 10 separating from the centrum 1 and the centrum 2 for hooking one end of a connecting member 7 such as an artificial ligament. A hook portion 9F is provided on an upper portion of the implant 9, and one end portion of the connecting member 7 is hooked over the hook portion 9F. Another end portion of the connecting member 7 is hooked over a hook portion 5F provided on one top end (the side engaged the first implant 3) of the connection rod 5.

Also, instead of using the connecting rod 5, the connecting member 7 may be used for connecting a first implant to a second implant. A first implant having a hook portion is screwed into the centrum 1, a second implant having a hook portion is screwed into the centrum 2, and both end portions of the connecting member 7 are hooked over the hook portion of the first implant and that of the second implant respectively.

According to the above-described method screwing the implant for a bone connector into the centrum for fixing a positional relation between vertebrae, it is necessary to precisely screw the implant into the centrum without damaging other portion. This method requires high technique and a burden of the centrum becomes large, because the implant is screwed into centrum.

SUMMARY OF THE INVENTION

The present invention has been proposed in view of the above-described circumstances, and it is an object of the present invention to provide an implant for a bone connector capable of being stably fixed to a vertebral arch of a vertebra without damaging the centrum.

In order to achieve the above object, the present invention provides an implant for a bone connector comprising: a fixing clamp to support a vertebral arch of a vertebra by grasping the vertebral arch; an implant body provided on an upper portion of the fixing clamp; and a hook portion, provided on an upper portion of the implant body, for hooking a connecting member which connects the implant with another implant.

According to the present invention, the fixing clamp is provided to a lower portion of the implant body, and supports the vertebral arch of a vertebra by grasping the vertebral arch. The hook portion is provided on the upper portion of the implant body, and the connecting member is hooked over the hook portion. Therefore, the implant is engaged with the vertebral arch and the connecting member. As a result, it is possible to stably fix the implant to the vertebral arch without damaging the centrum, and the implant can be used in the same manner as the conventional implant.

In a preferred embodiment of the present invention, the fixing clamp has a curved shape.

According to the embodiment, even if the fixing clamp has a curved shape, the fixing clamp can be engaged with the vertebral arch. Therefore, it is possible to stably fix the implant to the vertebral arch without damaging the centrum.

In a preferred embodiment of the present invention, the implant further comprises a movable clamp, provided on an upper portion of the implant body and disposed to be opposed to the fixing clamp, for grasping the vertebral arch of the vertebra.

According to the embodiment, the vertebral arch can be grasped from both sides of the vertebral arch by the fixing clamp and the movable clamp and be fixed to the implant. Therefore, it is possible to stably fix the implant to the vertebral arch without damaging the centrum.

In a preferred embodiment of the present invention, the movable clamp can be moved and adjusted in a direction approaching the fixing clamp and separating from the fixing clamp.

According to the embodiment, since the movable clamp can be moved freely in accordance with a size of the vertebral arch, the implant can strongly grasp the vertebral arch by means of the fixing clamp and the movable clamp, and be stably fixed to the vertebral arch without damaging the centrum.

In a preferred embodiment of the present invention, the movable clamp has a curved shape.

According to the embodiment, even if the movable clamp has a curved shape, the movable clamp can be engaged with the vertebral arch. Therefore, it is possible to stably fix the implant to the vertebral arch without damaging the centrum.

In a preferred embodiment of the present invention, fixing tools are provided to the implant body and the hook portion for fixing the movable clamp between the implant body and the hook portion.

According to the embodiment, it is possible to fix the movable clamp between the implant body and the hook portion without requiring new another parts.

In a preferred embodiment of the present invention, the fixing tools are a thread hole provided on an upper surface of the implant body and a thread portion provided on a lower portion of the hook portion.

According to the embodiment, it is possible to fix the movable clamp between the implant body and the hook portion only by adjusting the hook portion having the thread portion.

DESCRIPTION OF THE PREFERRED EMBODIMENT

Two embodiments of an implant for a bone connector according to the present invention will be explained in detail based on the drawings.

Figure 1:
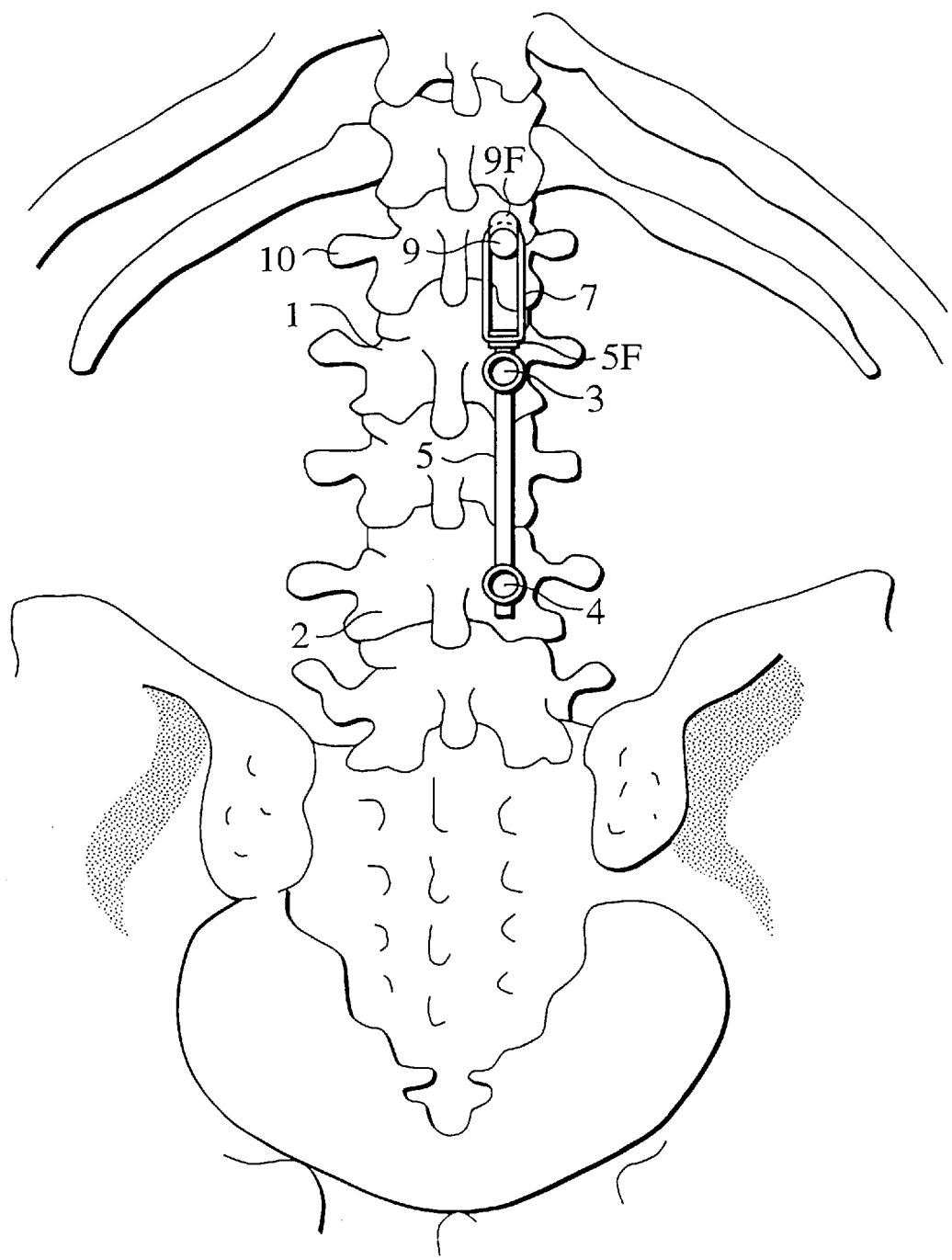
FIG. 1 is a schematic diagram of a conventional implant for bone connector.
Figure 2:
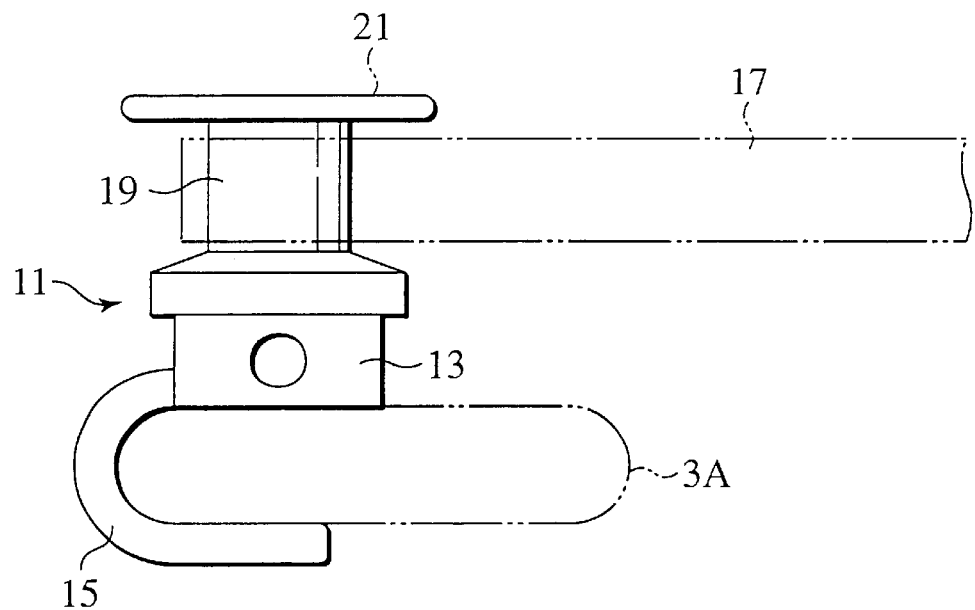
FIG. 2 is a front diagram of an implant for bone connector according to a first embodiment of the present invention.

FIG. 2 shows a first embodiment of the present invention. An implant 11 includes a block-like implant body 13, an U-shaped curved fixing clamp 15, a pin-like hook portion 19, and a flange portion 21. The fixing clamp 15 is provided to a lower portion of the implant body 13 for supporting a vertebral arch 3A of a vertebra by grasping the vertebral arch 3A. The hook portion 19 having a circular cross section is integrally provided on an upper portion of the implant body 13, and a connecting member 17 such as a wire or cable is hooked over the hook portion 19. The flange portion 21 is provided on an upper portion of the hook portion 19 for preventing the connecting member 17 from coming out.

In a state that the implant 11 is used for hooking the connecting member 17 over the hook portion 19 in the above configuration, since the implant 11 is fixed to the vertebral arch 3A by means of the fixing clamp 15 to support the vertebral arch 3A by grasping it and the connecting member 17 is hooked over the hook portion 19 of the implant 11, it can be used in the same manner as a conventional implant.

With such a configuration, the implant 11 is not screwed into the centrum, and is fixed to the vertebral arch 3A by means of the fixing clamp 15. Therefore, a burden of the centrum can be lightened.

Figure 3:
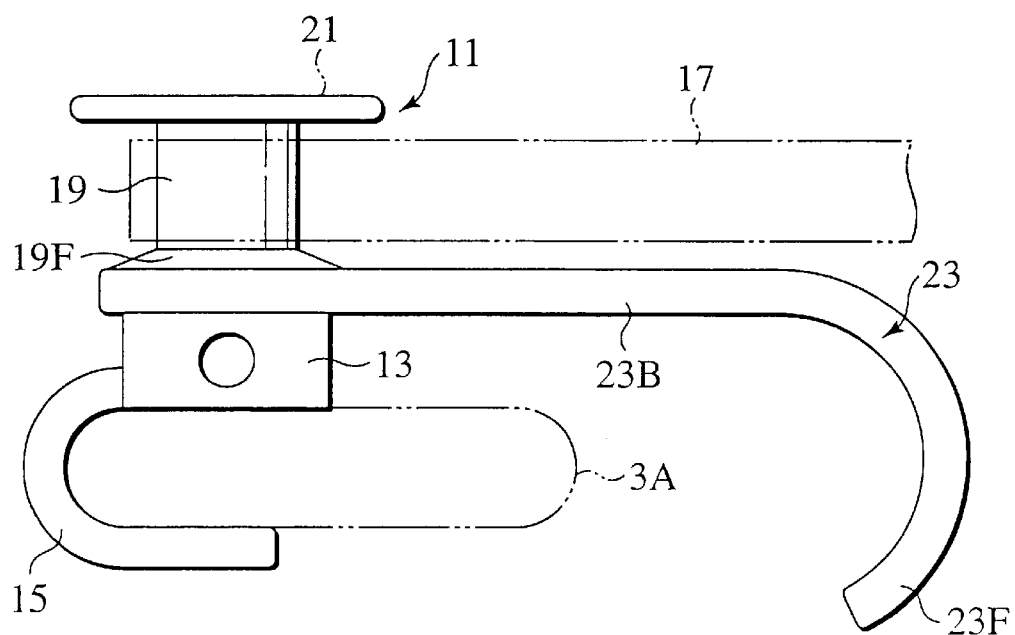
FIG. 3 is a front diagram of an implant for bone connector according to a second embodiment of the present invention.
Figure 4:
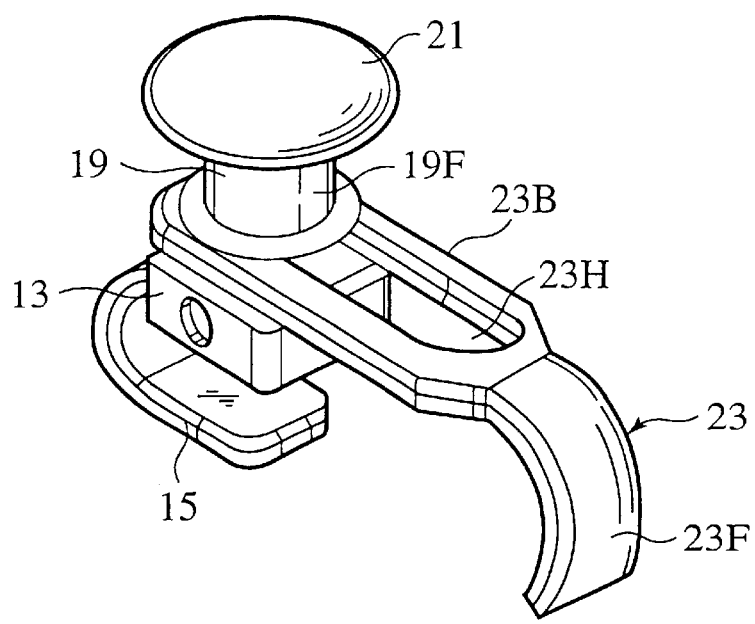
FIG. 4 is a perspective diagram of the implant for bone connector according to the second embodiment of the present invention.
Figure 5:
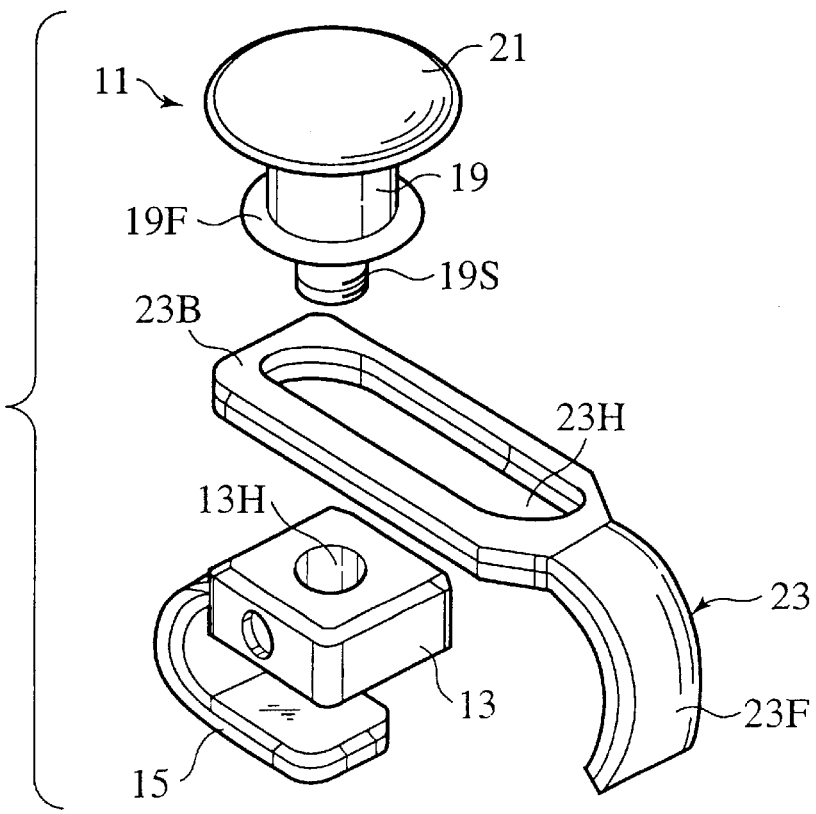
FIG. 5 is an exploded perspective diagram of the implant for bone connector according to the second embodiment of the present invention.

FIGS. 3 to 5 show a second embodiment of the present invention. In an implant 11 of this embodiment, a movable clamp 23, which is disposed to be opposed to the fixing clamp 15 and which grasps the vertebral arch 3A, is provided on an upper portion of the implant body 13. The movable clamp 23 can be freely slid and turned or fixed.

More specifically, as shown in FIG. 5, a thread hole 13H is formed on an upper surface of the implant body 13 having the fixing clamp 15, and a thread portion 19S which is screwed into the thread hole 13H is provided on a lower portion of the hook portion 19. The movable clamp 23 includes the curved hook portion 23F on a tip end of a clamp body 23B. Further, the clamp body 23B has a slit or a long hole 23H. Since the movable clamp 23 is disposed to be opposed to the fixing clamp 15, the hook portion 23F grasps the vertebral arch 3A of the vertebra at the opposed side of the fixing clamp 15.

In the above configuration, as shown in FIG. 5, the clamp body 23B of the movable clamp 23 is disposed between the implant body 13 and the hook portion 19 and then, the thread portion 19S of the hook portion 19 is allowed to pass through the long hole 23H formed in the clamp body 23B and to be screwed into the thread hole 13H of the implant body 13. Then, the movable clamp 23 is sandwiched between the implant body 13 and the hook portion 19.

In a state in which the movable clamp 23 is softly sandwiched between the implant body 13 and the hook portion 19, the movable clamp 23 can be moved and adjusted in a direction approaching the fixing clamp 15 and separating from that, and the movable clamp 23 can be rotated and adjusted around the thread portion 19S of the hook portion 19. Therefore, the movable clamp 23 can be adjusted to a size of the vertebral arch 3A. If the thread portion 19S of the hook portion 19 is strongly fastened to the thread hole 13H, the clamp body 23B of the movable clamp 23 is strongly sandwiched and fixed between the implant body 13 and a lower flange 19F provided on a lower portion of the hook portion 19. Therefore, the implant 11 can firmly grasp the vertebral arch 3A of the vertebra from both sides of the vertebral arch 3A by means of the fixing clamp and the movable clamp. That is, in this embodiment, the hook portion 19 serves as a hook over which the connecting member 17 is hooked, and as a fixing tool for fixing the movable clamp 23.

Since the implant 11 firmly grasps the vertebral arch 3A from both sides of the vertebral arch 3A by means of the fixing clamp 15 and the movable clamp 23, the implant 11 can be fixed to the centrum. Therefore, the same effect as the implant 11 of the first embodiment can be obtained, and the implant can be fixed to the centrum more stably.

Figure 6:
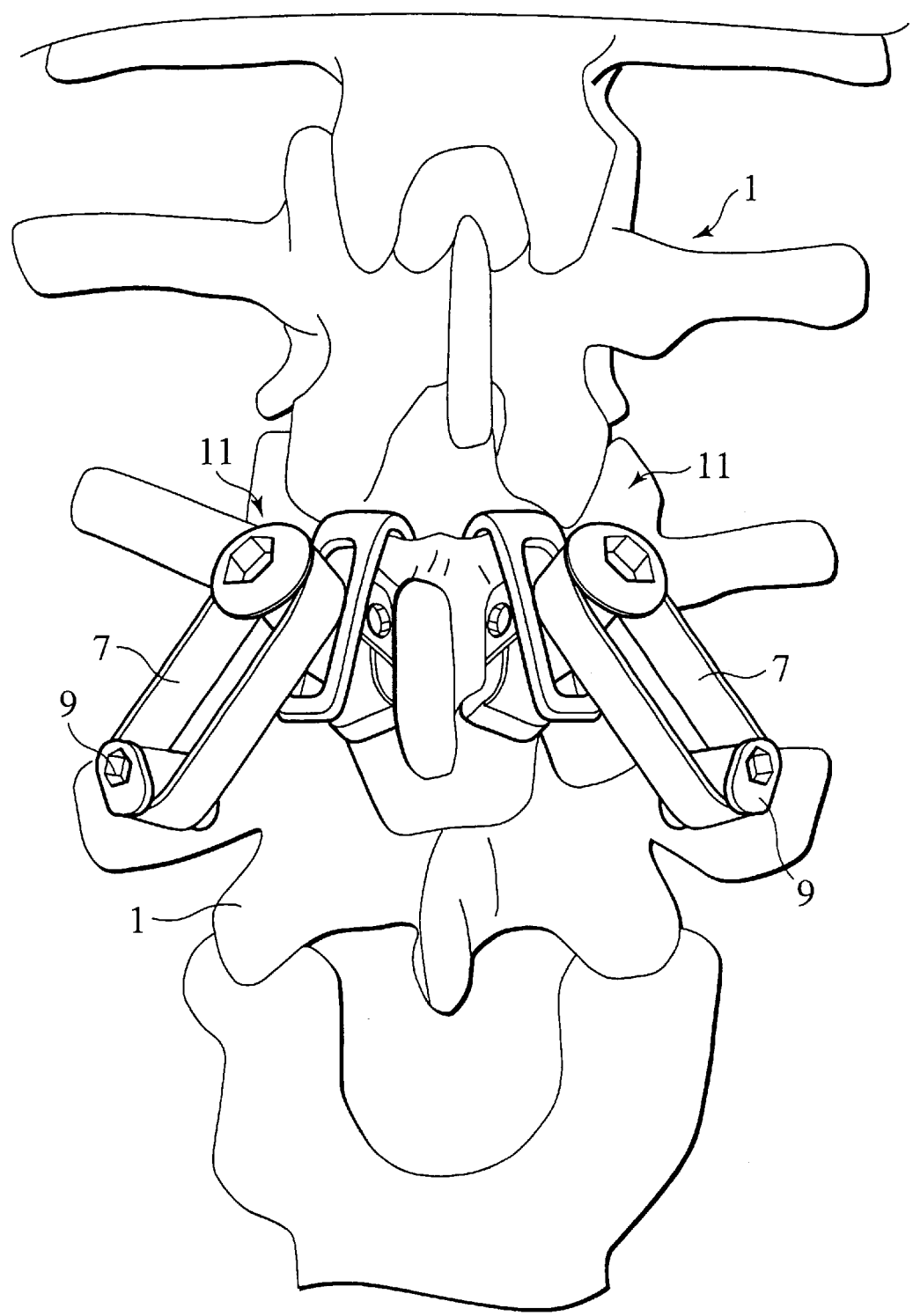
FIG. 6 is a diagram showing one using example of the present invention.

FIG. 6 shows one example in which the connecting member 7 is hooked over the implant 11 and the implant 9. In this case, the implant 9 which is screwed into centrum is used instead of the implant 11.

The above-described embodiment is one example of the present invention. Thus, the present invention is not limited to the above embodiment, and various modifications can be made in accordance with configuration within a range not departing from technical idea of the invention.

That is, although both the fixing clamp and moving clamp have curved shapes respectively in the two embodiments, the present invention is not limited to this, and the invention can be applied only if the vertebral arch 3A of the vertebra can be grasped.

What is claimed is:

1. An implant for a bone connector comprising:
   a fixing clamp to support a vertebral arch of a vertebra by grasping the vertebral arch;
   an implant body provided on an upper portion of the fixing clamp;
   a movable clamp disposed to be opposed to the fixing clamp for grasping the vertebral arch of the vertebra;
   a hook portion, provided on an upper portion of the implant body, for hooking a connecting member which connects the implant with another implant;
   a first fixing tool provided on the implant body; and
   a second fixing tool provided on the hook portion,
   wherein the movable clamp is fixed between the implant body and the hook portion by connecting the first fixing tool and the second fixing tool together.

2. An implant for a bone connector according to claim 1, wherein the fixing clamp has a curved shape.

3. An implant for a bone connector according to claim 1, wherein the movable clamp can be moved and adjusted in a direction approaching the fixing clamp and separating from the fixing clamp.

4. An implant for a bone connector according to claim 1, wherein the movable clamp has a curved shape.

5. An implant for a bone connector according to claim 1, wherein the first fixing tool is a thread hole provided on an upper surface of the implant body and the second fixing tool is a thread portion provided on a lower portion of the hook portion.

* * * * *